(12) United States Patent
Overturf et al.

(10) Patent No.: US 6,733,976 B2
(45) Date of Patent: May 11, 2004

(54) DETECTION OF BACTERIAL KIDNEY DISEASE

(75) Inventors: Kenneth E. Overturf, Buhl, ID (US); Madison S. Powell, Twin Falls, ID (US)

(73) Assignees: Idaho Research Foundation, Moscow, ID (US); The United States of America as represented by the Secretary of Agriculture, Washington, DC (US)

(*) Notice: Subject to any disclaimer, the term of this patent is extended or adjusted under 35 U.S.C. 154(b) by 41 days.

(21) Appl. No.: 10/206,261

(22) Filed: Jul. 25, 2002

(65) Prior Publication Data

US 2004/0018496 A1 Jan. 29, 2004

(51) Int. Cl.[7] .......................... C12Q 1/68; C12P 19/34; C07H 21/04; C07K 14/195
(52) U.S. Cl. .................. 435/6; 435/91.2; 536/23.1; 536/23.7; 536/24.32; 536/24.33; 536/25.32; 530/350
(58) Field of Search .................. 435/6, 91.2; 536/23.1, 536/23.7, 24.32, 24.33, 25.32; 530/350

(56) References Cited

U.S. PATENT DOCUMENTS 6,171,785 B1    1/2001    Higuchi

OTHER PUBLICATIONS

McIntosh, D. et al. A simplified PCR–based method for the detection of *Renibacterium salmoninarum* utilizing preparations of rainbow trout (*Oncorhynchus mykiss*, Walbaum) lymphocytes. Applied and Environmental Microbiology 62(11):3929–3932 (Nov. 1996).*

Miriam, A. et al. PCR and probe–PCR assays to monitor broodstock Atlantic salmon (*Salmo salar* L.) ovarian fluid and kidney tissue for presence of DNA of the fish pathogen *Renibacterium salmoninarum*.Journal of Clinical Microbiology 35(6):1322–1326 (Jun. 1997).*

Brown, L.L. et al. Use of the polymerase chain reaction (PCR) to detect DNA from *Renibacterium salmoninarum* within individual salmonid eggs. Diseases of Aquatic Organisms 18(3):165–171 (Apr. 1994).*

Cook, M. et al. A sensitive nested reverse transcriptase PCR assay to detect viable cells of the fish pathogen *Renibacterium salmoninarum* in Atlantic salmon (*Salmo salar* L.). Applied and Environmental Microbiology 65(7):3042–3047 (Jul. 1999).*

Chien, M.S. et al. Molecular cloning and sequence analysis of the gene coding for the 57–kDa major soluble antigen of the salmonid fish pathogen *Renibacterium salmoninarum*. FEMS Microbiology Letters 96:259–266 (1992).*

(List continued on next page.)

*Primary Examiner*—Diana B. Johannsen
(74) *Attorney, Agent, or Firm*—Howard Eisenberg, Esq.

(57) ABSTRACT

A real-time PCR method for detecting and quantifying the presence or absence of *Renibacterium salmoninarum*, the causative organism of Bacterial Kidney Disease, in a sample. The method includes the steps of combining with a sample a pair of PCR primers that bind to a DNA that is specific for the organism and a labeled probe that also binds to the DNA, and performing one or more rounds of PCR on the sample. The probe undergoes a change with each round of amplification of the DNA during the PCR reaction, which change causes a change in the signal provided by the label, thus providing a detection of the DNA and, if desired, a quantification, of the level of the DNA, and thus the level of the organism, in the sample.

16 Claims, 5 Drawing Sheets

OTHER PUBLICATIONS

Elliott, D.G. et al. The role of biotechnology in the detection of *Renibacterium salmoninarum* infections in salmonid fishes—promises and pitfalls. Bulletin of the Aquaculture Association of Canada 100–3:6–12 (Dec. 2000).*

Rhodes, L.D. et al. Sensitive detection of *Renibacterium salmoninarum* in whole fry, blood, and other tissues of Pacific salmon by reverse transcriptase–polymerase chain reaction. Molecular Marine Biology and Biotechnology 7(4):270–279 (Dec. 1998).*

Grove, D.S. Quantitative real–time polymerase chain reaction for the core facility using TAQMAN and the Perkin–Elmer/Applied Biosystems Division 7700 sequence detector. Journal of Biomolecular Techniques 10(1):11–16 (Mar. 1999).*

Newton, C.R. "Chapter 6: Primers." PCR Essential Data, C.R. Newton, ed., John Wiley & Sons, Chichester, 1995, pp. 49–56.*

Ahern, H. Biochemical, reagent kits offer scientists good return on investment. The Scientist 9(15):20 (Jul. 1995).*

Bullock, GL and Herman, RL, "Bacterial Kidney Diseases of Salmonid Fishes Caused by *Renibacterum salmoninarum*", Fish Disease Leaflet 78, United States Department of the Interior (1988), (vol / pages N/A).

European Commission: Health & Consumer Protection Directorate–General, "Bacterial Kidney Disease", Report of the Scientific Committee on Animal Health and Animal Welfare (1999), (vol / pages N/A).

Ryman, N., and Jorde, PE, "Statistical Power when Testing for Genetic Differentiation", Molecular Ecology, 10:2361–2373 (2001).

Starliper, CE, "Evaluation of the Genetic Diversity of *Renibacterium salmoninarum*", U.S. Geological Survey Biological Information & Technology Notes, No. 97–005 (1997), (vol / pages N/A).

* cited by examiner

DETECTION OF BACTERIAL KIDNEY DISEASE

FIELD OF THE INVENTION

The invention pertains to the field of detection of the presence of a pathogenic organism in the environment and in tissues of susceptible individuals. In particular, the invention pertains to the detection of the presence of the causative organism of Bacterial Kidney Disease (BKD) of salmonids.

BACKGROUND OF THE INVENTION

Bacterial Kidney Disease (BKD) is a disease of salmonids, such as salmon and trout species. BKD is a systemic illness that causes high mortality. The course of the disease is typically chronic, although acute outbreaks also occur. The disease was first reported in Scotland in 1931 and has since been reported in many countries around the world, including the United States, Canada, Chile, England, France, Germany, Iceland, Italy, Japan, Spain, Turkey, and in the Balkan peninsula.

BKD is a slowly progressing systemic illness in which the clinical signs typically are not evident until the disease is well established. External signs typically include exophthalmos and small closed blebs or open lesions. The unruptured blebs contain fluid composed of blood cells and necrotized tissue. In advanced cases, the lesions may coalesce and form large shallow ulcers. Internally, the kidneys are the organs most often affected. They become swollen and show discrete white areas that contain leucocytes, bacteria, and host cell debris. In advanced cases much kidney tissue is destroyed and hematopoietic and excretory functions are both affected. Hemorrhages occur in the body wall and testes, and peritoneal fluid is commonly present. The hind gut can be hemorrhagic and filled with white or yellow viscous fluid.

Death due to BKD most commonly is sporadic and occurs over a long period of time, although subacute outbreaks with 25 to 50% mortality occurring within a few weeks have been reported. Juvenile salmonids show the greatest susceptibility to infection with the level of susceptibility being highly variable between species. Inapparent carriers of the disease are common, as infected fish may carry the causative organism of the BKD for years without showing any clinical signs. The disease may only manifest itself clinically when such carrier fish are stressed.

The causative organism of BKD is a slow-growing gram positive bacterium, *Renibacterium salmoninarum*. This bacterium lives both extracellularly and intracellularly in the salmonid host and has been shown to survive and even to multiply within macrophages. This permits the bacterium to spread readily throughout the body. The intracellular location and the widespread distribution of *R. salmoninarum* within the body make the infection difficult to treat because antibiotics may not reach all of the locations where the organism resides. Antibiotics typically employed, such as erythromycin, are cleared rapidly by the fish and require administration at near toxic levels. Additionally, BKD disease is one of the few bacterial diseases that can be spread both horizontally and vertically. *R. salmoninarum* can be transmitted in the egg.

Because of the widespread systemic distribution and intracellular location of the BKD bacterium, the presence of latent carriers, the ability of the disease to be transmitted vertically, and the lack of an effective bacterin, BKD has proven to be very difficult to control. Therefore, because of the potential for BKD to devastate a population, control efforts are concentrated in preventing exposure of infected fish to the BKD organism. It is common practice to isolate salmon returning to hatcheries, segregate fertilized eggs until diagnostic test results are evaluated, test each female, cull eggs from females with test results that suggest the presence of the BKD organism, and segregate remaining progeny according to the test values of the females.

Presently available tests for the BKD organism present problems that have not as yet been overcome. The isolation and identification of *R. salmoninarum* in samples from clinically infected fish is relatively easy. However, the slow growth of the organism and the fact that *R. salmoninarum* is a fastidiously growing organism requiring prolonged incubation at 15° C. to produce colonies renders such tests of little utility in practice. Thus, serological methods are more usually employed to confirm the presence of the bacterium.

Immunofluorescence antibody tests (FAT) have commonly been used for demonstrating the presence of *R. salmoninarum* in infected tissues. Screening of ovarian fluid from asymptomatic brook trout populations using FAT and ELISA found that twice as many positives were detected using a FAT method than by ELISA. However, FAT reproducibility is poor for very low levels of infection, resulting in some infections being missed.

ELISA is widely used for the detection of *R. salmoninarum*, and several commercial kits are available. The most common technique used is a double antibody sandwich ELISA method. Samples of tissue (fish kidneys) collected for examination must be kept cold or frozen after collections. Tissues from clinically and sub clinically infected fish have ELISA reactions that are clearly distinct from those of uninfected fish. Unfortunately, ELISA does not work well on ovarian or seminal fluid. Since the ELISA test is performed on kidney tissue, diagnosis is not possible until after stripping eggs from the females. This requires extra manpower and space in order to strip eggs from females that will test above the culling threshold and to keep eggs segregated by female until the ELISA results are evaluated. There is about a four (4) week delay from submitting samples to a lab and receiving results. While several ELISA methods are available, it is important to note that the various evaluations as to their sensitivity and specificity have not been uniformly carried out.

Polymerase Chain Reaction (PCR) has been used for the detection and identification of *R. salmoninarum* directly within ovarian fluid or individual eggs. Present techniques rely on detection of DNA segments of the gene coding for the antigenic p57 protein. The nucleotide sequence coding for this protein is available from GenBank at the National Center for Biotechnology Information (NCBI) of the National Institutes of Health (NIH) and has been assigned Accession No. AF123888. These PCR methods are very sensitive and have a high degree of specificity. The PCR/ovarian fluid method does not detect significantly more positives than ELISA methods from the kidneys, but is more rapid as results are obtained within 1 to 2 days and, in contrast to ELISA which utilizes kidney tissues, is non-lethal as,ovarian test fluid may be obtained when stripping eggs. Other studies have found PCR to identify higher numbers of kidney tissue and ovarian fluid samples from commercially reared brood stock fish to be positive for *R. salmoninarum* than were identified by culture.

One potential problem with PCR diagnostic methods is that a PCR-positive sample may contain some proportion of dead *R. salmoninarum* with detectable levels of DNA, such as due to previous antibiotic therapy or fish that have conquered the disease. Other problems that occur when using standard PCR methods include incorrect interpretation of band presence or absence because of improper primer annealing or buffer concentration. Additionally, the number of cycles to run for correct band amplification can vary between the primers and the type of machine used. These problems are further exacerbated when attempts are made to quantify the level of bacteria present. For *R. salmoninarum*, this has proven even more difficult with the necessary use of nested PCR for detection of the pathogen, since the addition of extra primers and increased cycle numbers leads to an increase in the detection of false positive bands.

In recent years, PCR methods have been adapted to provide both for detection and for quantification of nucleic acid sequences in a sample. For example, see, Higuchi, U.S. Pat. No. 6,171,785, incorporated herein by reference. These methods employ forward and reverse primers as in standard PCR plus one or more additional nucleic acid sequences that hybridize to the nucleic acid that is to be amplified. This additional nucleic acid sequence, termed a "probe", hybridizes to a portion of the nucleic acid to be amplified between the portions that hybridize to the two primers, and is labeled in such a way so that each successive PCR cycle causes a change in the probe or its label. This change in the probe or its label causes activation or accentuation of the label to a degree that is related to the number of additional copies of the amplified nucleic acid during each PCR cycle. By utilizing such methods, referred to as "real-time" PCR, cycle-by-cycle detection of increasing PCR product is achieved by combining thermal cycling with label detection.

Most commonly, the label for the probe is a fluorescent label which provides a fluorescent output signal. This may be achieved by providing a probe which is double-labeled with a flourescent reporter dye at one end, typically the 5' end, and a quencher dye at the other, the 3', end. When the probe is intact, the proximity of the quencher dye to the reporter dye suppresses the fluorescent output of the reporter dye. During each PCR cycle, the 5' nuclease activity of a DNA polymerase cleaves the probe, which separates the reporter dye from the quencher dye. This separation results in increased fluorescent output of the reporter dye.

During PCR, if the target of interest is present in a sample, the probe will specifically anneal between the forward and reverse PCR primer sites. The nucleolytic activity of the DNA polymerase cleaves the probe between the reporter and the quencher dyes only if the probe hybridizes to the target molecule. The increase in fluorescence is detected only if the target sequence is complementary to the probe and is amplified during PCR. Because of these requirements, non-specific amplification is not detected. Only amplified products that contain the sequence complementary to the probe are recognized by the presence of the fluorescent signal, thereby eliminating certain elements related to the analysis of false-positives. Additionally, one or more other enzymes may be utilized to help limit the amplification of carry over transcription products.

This type of quantitative PCR permits the normalization of pipetting errors and volume changes, which may be done by dividing the reporter fluorescence by a passive reference, contained within each reaction, to determine the normalized reporter signal for each individual reaction. Software may be used to analyze the cycle-to-cycle increase in fluorescence intensity and compare this data to standards in order to determine starting copy numbers for absolute quantification or to compare against other unknown samples for a comparison of relative quantity.

To date, no such real-time method of detection of *R. salmoninarum* infection has been reported. The existence of such a method would have a significant impact on the ability to control this disease.

SUMMARY OF THE INVENTION

In one embodiment, the invention is a method for detection of the causative organism of Bacterial Kidney Disease (BKD) in a sample using real-time polymerase chain reaction (PCR). According to this embodiment, a forward primer, a reverse primer, which primers anneal to a DNA sequence that is specific to the *Renibacterium salmoninarum* genome, a labeled probe, which probe anneals to the DNA at a site between the sites of annealing of the forward and reverse primers, a DNA polymerase, and the four deoxynucleotide bases A, T, C, and G are combined with a test sample to form a mixture. The mixture is taken through successive (PCR) cycles, wherein the probe contains a label that is activated or accentuated to a degree that is related to the number of additional copies of the amplified nucleic acid during each PCR cycle. The PCR cycles include the steps of adjustment to a temperature at which the DNA is separated into single strands, adjustment to a temperature at which the primers and the probe anneal to complementary sequences on the DNA, and adjustment to a temperature at which the polymerase binds and extends a complementary DNA strand from each primer.

In another embodiment, the invention is a method for detection of the causative organism of Bacterial Kidney Disease (BKD) in a sample using real-time polymerase chain reaction (PCR). According to this embodiment, RNA in the sample is isolated and reverse transcribed to produce a cDNA. The cDNA is combined with a forward primer, a reverse primer, which primers anneal to a DNA sequence that is specific to the *Renibacterium salmoninarum* genome, a labeled probe, which probe anneals to the DNA at a site between the sites of annealing of the forward and reverse primers, a DNA polymerase, and the four deoxynucleotide bases A, T, C, and G to form a mixture. The mixture is taken through successive (PCR) cycles, wherein the probe contains a label that is activated or accentuated to a degree that is related to the number of additional copies of the amplified nucleic acid during each PCR cycle. The PCR cycles include the steps of adjustment to a temperature at which the DNA is separated into single strands, adjustment to a temperature at which the primers and the probe anneal to complementary sequences on the DNA, and adjustment to a temperature at which the polymerase binds and extends a complementary DNA strand from each primer. This embodiment is especially preferred if is it desired to determine the viability of the organism in the sample.

In another embodiment, the invention is a primer that binds to a DNA sequence that is specific to the *Renibacterium salmoninarum* genome, which primer, when combined with the DNA, a second primer that binds to the DNA, a DNA polymerase, and the four deoxynucleotide bases A, T, C, and G, provides exponential expansion of copies of the DNA during successive rounds of PCR. Preferably, the DNA sequence is a portion of the genome of *Renibacterium salmoninarum* that codes for the p57 protein. In a preferred embodiment, the primer has the sequence 5'-CAACAGGGTGGTTATTCTGCTTTC-3', designated as Seq. ID No. 1. In another preferred embodiment, the primer has the sequence 5'-CTATAAGAGCCACCAGCTGCAA-3', designated as Seq. ID No. 2.

In another embodiment, the invention is a kit that is useful for the detection of *Renibacterium salmoninarum*, the causative organism of BKD, in a sample.

BRIEF DESCRIPTION OF THE DRAWINGS

FIG. 1 shows a 95 bp oligonucleotide sequence spanning the entire probe/primer region, which is designated as Seq. ID No. 4.

DETAILED DESCRIPTION OF THE INVENTION

Figure 1:
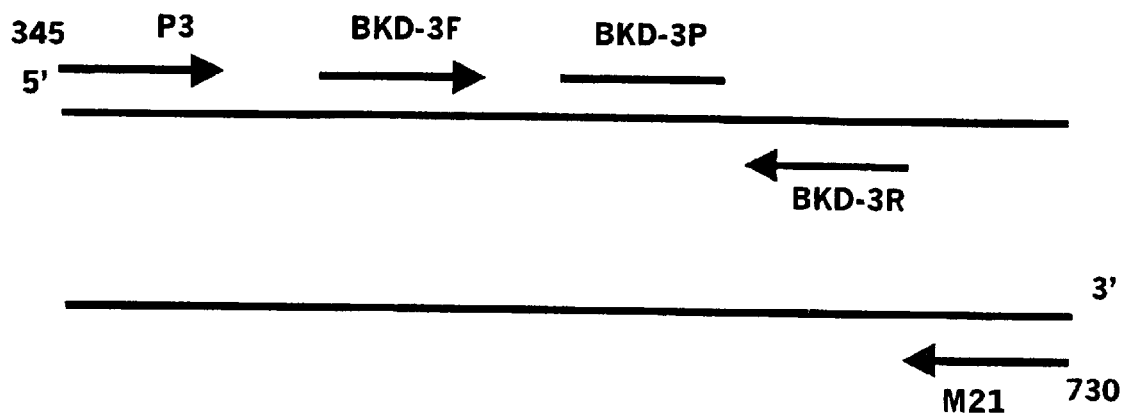
FIG. 1 is a diagrammatic representation showing the placement of the preferred primers and probe of the invention on the p57 gene in relation to the primers used for nested PCR.

The methods and kits of the present invention are directed to the detection of the causative bacterial organism of Bacterial Kidney Disease (BKD) in a sample, and preferably to the quantification, either absolute or relative, of the bacteria in the sample. Detection of the bacteria by the methods and kits of the invention is based upon detection of a nucleotide sequence specific to the genome of *Renibacterium salmoninarum*. The invention permits the detection of the bacteria in infected fish, as well as in the environment, such as in water, feed, and other reservoirs of infection. The ability to quantify the bacteria provides for the ability to determine changes in the abundance of the BKD organism over time.

The compositions of the present invention are nucleotide sequences that are primers or probes for the detection of *Renibacterium salmoninarum* by PCR, and preferably by real-time PCR, methods. The primers and probes of the invention hybridize to a nucleotide sequence that is specific to the genome of the bacteria. In a preferred embodiment, the nucleotide sequence is a portion of the gene that codes for the p57 protein of *R. salmoninarum*, which sequence is available from GenBank at the National Center for Biotechnology Information (NCBI) of the National Institutes of Health (NIH), Accession No. AF123891. Preferably, the probes and primers of the invention hybridize to portions of the p57 gene, although probes and primers may hybridize to other DNA sequences specific to the genome of *R. salmoninarum*, such as to the DNA sequences assigned GenBank Accession Nos. AF123888, AF428065 to AF428072, AF178994, X76499, AF245384 to AF245386, and AF242882 to AF242889.

Methods of PCR and real-time PCR are known in the art. Additionally, other methods of PCR and real-time PCR may be developed in the future and it is intended that such methods be included as suitable for the methods and kits of the invention, so long as such methods are used to detect, preferably quantitatively, the presence or absence of the BKD bacteria in a sample.

According to the method of the invention, a pair of DNA sequences, hereafter referred to as "PCR primers" and a third DNA sequence, referred to as a "probe" are exposed to a sample DNA under conditions in which complementary DNA strands will hybridize and the primers and the probe are permitted to either hybridize or not hybridize to two separated portions of the DNA. The primers and the probe bind specifically to a DNA that is specific to the genome of the BKD bacteria. The primers bind to separated portions of the DNA and the probe binds to a portion of the DNA that is between the portions of the DNA that bind to the primers. The primers, the probe, and the DNA sequence are then exposed to conditions in which the DNA is replicated and then to conditions in which the DNA is denatured. Preferably, multiple cycles of annealing, extension, and denaturation ("PCR cycle") are performed. By this method, if a DNA that is complementary to the two primers exists in the sample, multiple copies of the DNA are obtained.

The probe is itself a label or contains a label. Each successive PCR cycle causes a change in the probe or its label. This change in the probe or its label causes activation or accentuation of the label to a degree that is related to the number of additional copies of the amplified nucleic acid during each PCR cycle. By utilizing such methods, referred to as "real-time" PCR, cycle-by-cycle detection of increasing PCR product is achieved by combining thermal cycling with label detection.

Preferably, the label is a fluorescent label that increases in intensity to a degree that is related to the number of copies of the DNA that are produced during each PCR cycle. In a preferred embodiment, the probe is a DNA sequence that hybridizes to a portion of a DNA that is specific to the genome of the BKD bacteria at a position between the portions of the DNA where a forward and reverse PCR primer anneal to the DNA, which probe contains a fluorescent reporter dye and a quencher dye, preferably at opposite ends of the probe. The presence of the quencher dye and the reporter dye on the probe causes suppression of the fluorescence caused by the reporter dye. During the extension portion of each PCR cycle, the probe is cleaved, typically by action of a DNA polymerase, which separates the reporter and the quencher dyes, thereby causing an increase in fluorescence which is related to the number of copies of the DNA that are produced during each PCR cycle. The amount of fluorescence is determined after a known number of PCR cycles, which provides a quantitative measure of the number of copies of the DNA that was present in the cycle before PCR.

Because the increase in fluorescence signal is detected only if the target sequence is complementary to the probe, non-specific amplification is not detected by the method of the invention. Only amplified products that contain a sequence that is complementary to the probe are recognized by the giving off of a fluorescent or other signal, false-positives, which are a common problem with standard, non-real time PCR, are eliminated. Software may be used to analyze the cycle-to-cycle increase in fluorescent intensity and to compare this data to standards in order to determine starting copy numbers or to absolutely or relatively quantify the viral sequence present in the sample.

The invention is illustrated below with reference to a particular portion of a particular gene of the BKD bacteria and to particular DNA sequences, including particular primers and probes. One skilled in the art will understand that the invention is applicable to genes of *R. salmoninarum* other than those exemplified below and that primers and probes other than those disclosed herein, the DNA sequence of which other primers and probes may be determined by methods disclosed herein, may be used in accordance with the invention.

In accordance with the method of the invention, a DNA sequence that is particular to the genome of R. salmoninarum is amplified by PCR, preferably by real-time polymerase chain reaction to provide quantification of the number of copies of the DNA sequence that is present in a sample.

In accordance with a preferred embodiment of the invention, the DNA sequence that is determined to be present is the p57 gene. When performing the method of the invention to determine the presence in the sample of the this gene, a preferred forward primer has the sequence:

5'-CAACAGGGTGGTTATTCTGCTTTC-3', Seq. ID No. 1, a preferred reverse primer has the sequence:

5'-CTATAAGAGCCACCAGCTGCAA-3', Seq. ID No. 2, and a preferred probe has the sequence:

5'-CTCCAGCGCCGCAGGAGGAC-3', Seq. ID No. 3.

To determine an alternative suitable forward primer having a sequence other than Seq. ID No. 1, a candidate DNA sequence is determined that will hybridize to a portion of the p57 gene of the BKD bacteria that is 5' to the positions where the primer of Seq. ID No. 2 and the probe of Seq. ID No. 3 anneal. One or more PCR cycles of annealing, extension, and denaturation are performed with a sample containing a known quantity of the p57 gene, the primer of Seq. ID No. 2, and the probe of Seq. ID. No. 3. Following PCR, the quantity of DNA that has been amplified is determined. The candidate forward primer is suitable for the method of the invention if it, together with the other necessary components for PCR, produced an exponential expansion of copy number of the DNA during each round of PCR. In this way, the suitability of any candidate forward primer may be determined.

If desired, such a PCR protocol may be performed in parallel to a PCR protocol using the primers and probe of Seq. ID Nos. 1 to 3, whereby the number of copies obtained by a given number of PCR rounds with a candidate forward primer is compared with that obtained by the same number of PCR rounds using the exemplified forward primer of Seq. ID No. 1.

Suitable reverse primers may be determined in a similar manner, but utilizing a candidate reverse primer, the primer of Seq. ID No. 1 as a forward primer, and the probe of Seq. ID No. 3. Likewise, suitable probes may be determined by utilizing the primers of Seq. ID Nos. 1 and 2 and a candidate probe.

Suitable primers and probes for the methods of the invention to determine the presence of the a gene of BKD other than the p57 gene may be obtained by designing a pair of primers that anneal to the desired gene and a probe that anneals to the gene at a position between the annealing sites of the two primers. The candidate primers and probe are suitable for the method of the invention if they, together with the other necessary components for PCR, produce an exponential expansion of copy number of the DNA during each round of PCR.

When performing the method of the invention so as to obtain a quantitative assessment of the amount of BKD bacteria, or a gene of the BKD bacteria, in a sample, the amplification of a test sample may be compared to the amplification of a control standard or series of standards to determine an absolute quantity of BKD in the test sample. Alternatively, the amplification of a test sample may be compared to the amplification of a second sample in order to determine a relative quantity of BKD bacteria in the two samples. The ability to quantify the BKD bacteria, either absolutely or relatively, is an improvement over standard PCR methods for sequence quantification. In the real-time method according to the invention, the relative measurements in the sequence detector occur during the log phase of amplification. In contrast, with standard PCR, such measurements occur at the end of the reaction when amplification has reached a plateau stage.

The present invention provides for one or more kits containing the elements required to detect the presence of the BKD bacteria in a sample using real-time PCR. The kit includes a container housing a forward primer which is a DNA sequence that binds, as described above, to a DNA that is particular to the genome of R. salmoninarum. The kit further includes a container housing a reverse primer which is a DNA sequence that binds, as described above, to the same DNA at a site that is distinct from the site at which the forward primer binds. The kit further contains a probe which is a nucleotide sequence that binds to a site on the DNA between the sites of binding of the reverse and forward primers, wherein the probe is labeled in such a way that the label is activated or accentuated during each cycle of PCR in an amount that is related to the number of additional copies of the DNA that are amplified during the cycle. The primers and probes described above may be housed in the same or in separate containers. The kit optionally contains additional components for carrying out PCR, such as dNTPs, a DNA polymerase, and a reverse polymerase, and instructions for performing PCR and/or real-time PCR.

The DNA preferably is all or a portion of the p57 gene of R. salmoninarum. The forward primer preferably has the sequence of Seq. ID No. 1. The reverse primer preferably has the sequence of Seq. ID No. 2 The probe preferably has the sequence of Seq. ID No. 3. However, any primer or probe that is suitable for the method of the invention, as described above, is suitable for the kit of the invention.

Preferably, the probe is labeled with a fluorescent label, the intensity of which increases to a degree related to the number of additional copies of the DNA that are made with each cycle of PCR. However, labels other than fluorescent labels are suitable for the kit and method of the invention, so long as the intensity of the label increases to a degree that is related to the number of additional copies of the DNA that are obtained with each cycle of PCR.

Optionally, the kit may contain one or more enzymes that are used in the real-time PCR method of the invention. The kit may also contain any additional materials needed to carry out the method of the invention, such as buffers, pipettes, nucleic acids, tubes, and the like.

The invention is illustrated by the following non-limiting examples.

EXAMPLE 1

Sample Preparation for ELISA (Prior Art)

Samples of kidney tissue, each approximately 1 gram, were collected from 430 spawning chinook salmon from 5 locations within Idaho. The samples were homogenized and diluted 1:4 (w/v) in 0.01 M phosphate-buffered saline at pH 7.4, containing 0.05% Tween 20 (PBS-T20). The samples were stored at −20° C. until examined using an enzyme-linked immunosorbent assay (ELISA) technique as described in Pascho et al., 1991; and Pascho et al., 1998) using HRP-conjugated antibody lots KPL #TA 025 and KPL #U, V, W, developed for Renibacterium salmoninarum (Kirkegard and Perry Laboratories, Gaithersburg, Md., USA).

EXAMPLE 2

DNA Isolation and Standardization

Genomic DNA was extracted from kidney tissue homogenates using methods modified from Sambrook et al.

(1989) and Hillis et al., (1996). Total genomic DNA was standardized in each sample to 20 ng/ml using a spectrophotometer (Biophotometer, Eppendorf, Westbury, N.Y., USA) set at 1 U $A_{260}$=50 µg/µl. A 95 bp oligonucleotide spanning the entire probe/primer region (See FIG. 1) was synthesized (Sigma Genosys, St. Louis, Mo., USA). Because the exact molecular weight and optical density at specific concentrations may be calculated, the oligonucleotide was used to generate standard curves and establish upper and lower boundaries of extinction coefficients for quantitative PCR analyses.

EXAMPLE 3
Quantitative PCR and RT-PCR

FIG. 1 shows the placement and position of the quantitative PCR primer/probe combination of Seq. ID Nos. 1 to 3 used as well as the position of nested PCR primers (prior art) that they were compared to. Quantitative PCR was carried out in 50 µl reactions containing 25 µl of master mix (2x, TAQMAN® Master Mix, ABI, Foster City, Calif., USA) 0.3 µM of each primer and 0.2 µM of double labeled probe and 5 µl of DNA template (at 20 ng/µl). Reactions were carried Out on an Applied Biosystems Model 7700 quantitative PCR instrument (Applied Biosystems, Foster City, Calif., USA).

EXAMPLE 4
Quantitative PCR (QT-PCR)

Figure 2:
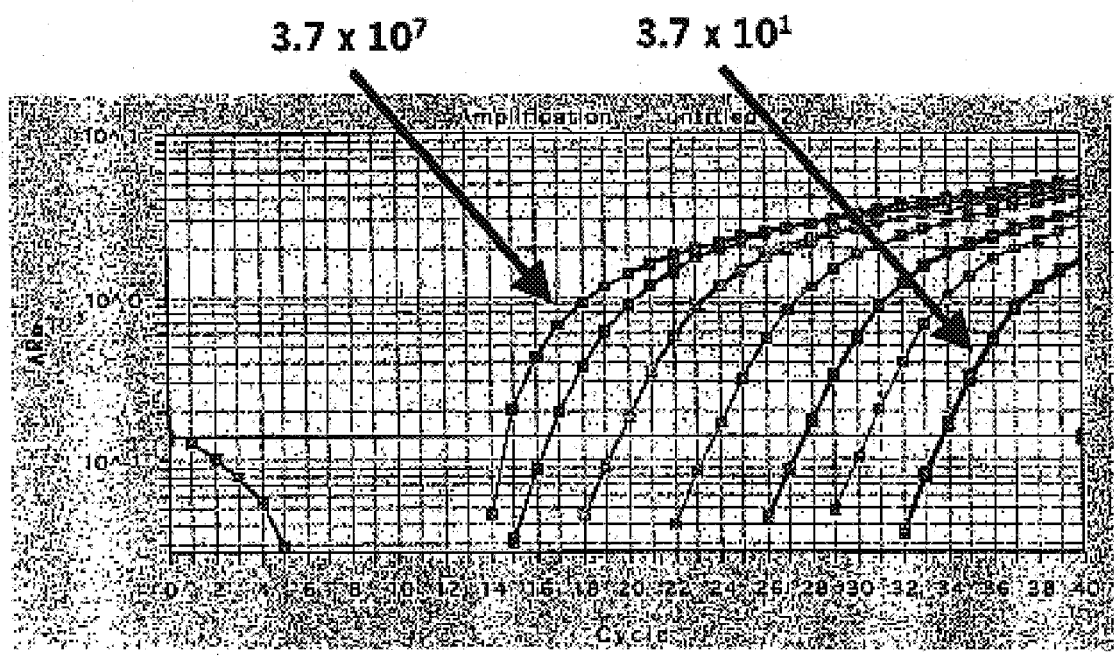
FIG. 2 is an amplification plot of the portion of the p57 gene amplified using the preferred primers and probe of the invention in serially diluted samples.

The change in fluorescent signal (ΔRN), normalized to a passive reference signal, for each cycle of amplification is shown in FIG. 2. Amplification products using the forward primer (Seq. ID No. 1, referred to in FIG. 1 as BKD-F3), the reverse primer (Seq. ID No. 2, referred to in FIG. 1 as BKD-R3), and double-labeled probe (Seq. ID No. 3, referred to in FIG. 1 as BKD-P3) yielded a 6-fold quantifiable range of estimated copy number, from 37 to 37,000,000 estimated copies. This result was obtained without significant increase in Ct values, also referred to as the threshold cycle, which corresponds to the cycle at which a statistically significant increase in fluorescent output occurs in relation to the starting quantity number, and without a significant increase in standard deviations.

Estimated copy numbers typically below 40 show increased Ct values and significant dispersion within standard deviations averaged among multiple replications. Therefore, for the primer set and technique described, the lower end of sensitivity of detection (coefficient of extinction) falls about 40–50 estimated copies. Conversely, depending on the amount of probe and primer used, the upper bound of estimated copy number (or template) is about 40,000,000 to 50,000,000 copies. Beyond this level, amplification does not proceed in an exponential fashion but becomes linear due to the overabundance of template DNA. Thus, estimates of copy number at very high levels may be inaccurate. However, concentrated samples may be serially diluted to minimize linear amplification and maximize exponential amplification, which will thus generate accurate copy number estimates.

Figure 3:
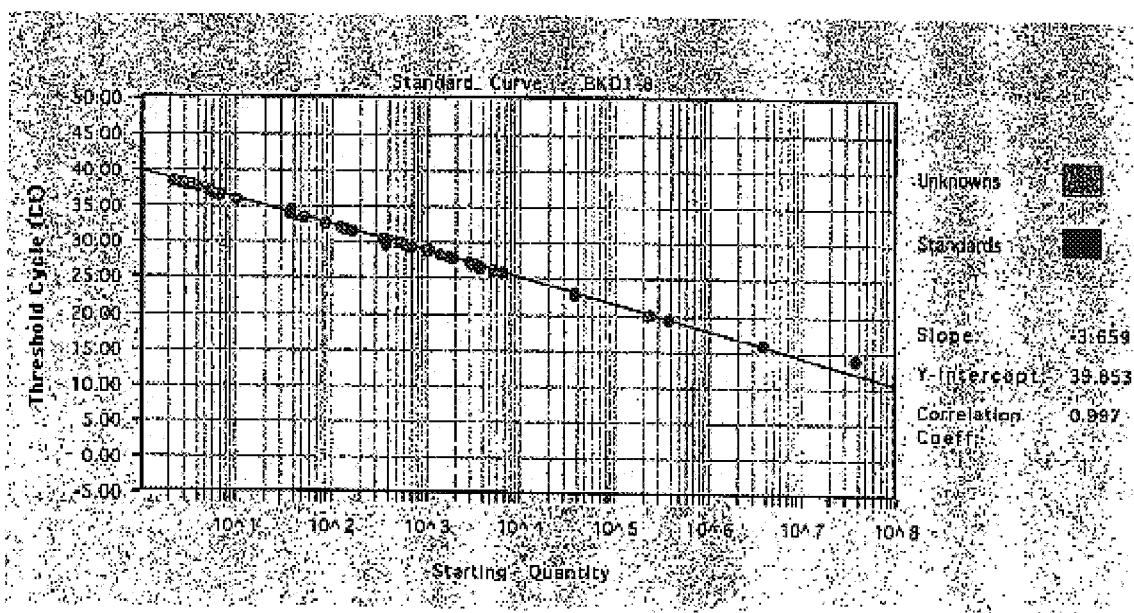
FIG. 3 is a standardization plot using various quantities of a 95-mer oligonucleotide portion of the p57 gene.

As shown in FIG. 3, standard curves generated using serial dilutions of the 95-mer oligonucleotide had high correlation coefficients, typically above 0.995. Unknowns were generally bracketed within the standard curve generated. Amplification that appeared to be below that used in the standard range were interpreted as "random amplification and fluorescent detection" and were interpreted as zero.

Figure 4:
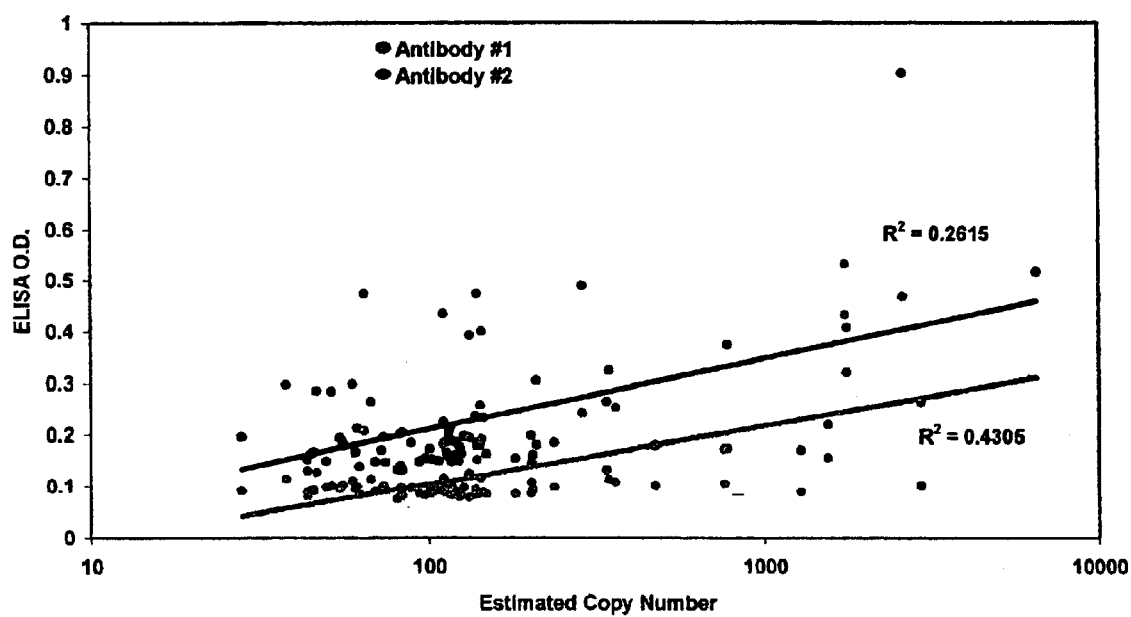
FIG. 4 is an graph showing the correlation of optical density measurements obtained using 2 different ELISA antibodies that bind to the p57 protein in comparison with estimated copy numbers obtained with the quantitative PCR method of the invention.

As shown in FIG. 4, quantitative PCR analyses according to the invention of 480 Chinook Salmon samples were compared to values obtained using ELISA with two separate antibody lots. Optical densities (O.D.) obtained with ELISA using antibody #1 had less dispersion about their linear regression than those obtained using antibody #2. However, both ELISA using either antibody showed a low correlation to estimated copy number, $R^2$=0.4305 and 0.2615, respectively, at the lower range of copy number and O.D. At higher levels of infection, above an O.D. of 0.5, optical densities from ELISAs using either antibody had high correlations (not shown), R2>0.8000, and followed an exponential rate of increase in estimated copy number.

EXAMPLE 5
QT-PCR Compared with Nested PCR (Prior Art)

Figure 5:
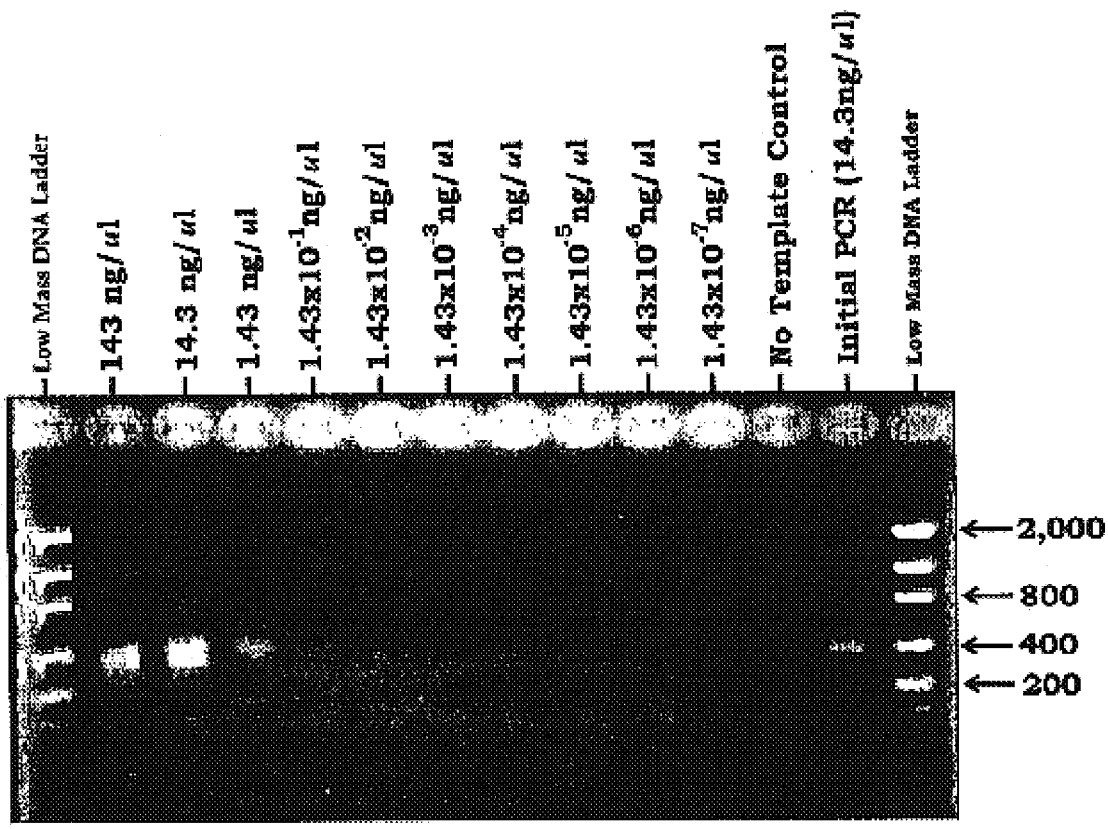
FIG. 5 is an ethidium bromide staining on agarose gel of serial dilutions of copies obtained following prior art nested PCR. Amplification products were visible to a four-fold dilution, to $1.43 \times 10^{-3}$ ng/ml.

FIG. 1 shows the placement of the preferred forward and reverse primers of Seq. ID Nos. 1 and 2 and of the preferred probe of Seq. ID No. 3 in relation to primers used for nested PCR analysis of BKD according to Pascho et al. (1998). FIG. 5 shows that the nested PCR amplification products for serial dilution of a BKD positive sample (ELISA O.D. 3.0) was detectable to lane 5, a four-fold logarithmic dilution of the sample so that the concentration in lane 5 was one ten thousandth that in lane 1.

In comparison, QT-PCR on the same set of dilutions yielded a quantifiable product to 6 logarithmic dilutions, to a concentration of one millionth that in lane 1. Accordingly, the QT-PCR method of the invention provided a 100-fold increase in sensitivity of BKD detection over the prior art nested PCR method.

The invention provides methods, kits, and nucleic acid sequences that are useful for monitoring and evaluating the presence of *Renibacterium salmoninarum*, the causative organism of Bacterial Kidney Disease, within a population and for appraising the carrier status of infected individuals. The speed and accuracy of the method make it especially useful for the detection of pathogenic organisms from non-symptomatic individuals.

In evaluating quantitative measurements of bacterial presence, the method of the invention is superior to known methods because, according to the invention, detection of the BKD organism is directly measured during the DNA amplification stage of PCR via a signal from a labeled probe which probe specifically identifies a sequence unique to the BKD bacteria. Advantages of the method of the invention over standard PCR detection methods is that no further steps are required for detection of minute quantities of BKD. Moreover, when using typical standard PCR for the detection of *R. salmoninarum*, single nested or dual nested PCR primers have been required for this detection, leading to increased levels of false negative bands and making it extremely difficult to perform any kind of quantitative analysis.

The use of a specifically labeled probe is another advantage of the invention as this helps to eliminate a problem associated with classic PCR methods of mispriming. In PCR protocols other than in accordance with the invention, PCR products are analyzed by the presence or absence of bands, and the presence of false priming sequences can lead to the amplification of non-target DNA. This problem is overcome according to the invention as a signal from the probe label is relayed only upon the amplification of a nucleic acid sequence that specifically hybridizes to the probe, and preferably upon cleavage of the probe upon such amplification.

The invention also provides a vast improvement in the determination of absolute quantities of BKD organisms. This is achieved by comparing the amplification and label output of an unknown sample at each PCR cycle to a series of standards and passive control sample signals that are preferably run concurrently with the unknown sample.

The improvement in quantification is also obtained in determining relative quantities of BKD bacteria. In this case, experimental samples are compared with each other and with a passive reference at each cycle rather than to a true standard.

The improvement in quantification by the method of the invention compared to standard, non-real-time, PCR is at least partially due to the fact that the absolute and relative measurements obtained according to the method of the invention are obtained during the log phase of amplification and not at the end of the reaction as with standard PCR, when amplification of sequences has reached a plateau state. Additionally, standard PCR may provide false information of quantity because, for example, if the number of cycles performed is too high, this may falsely elevate low level numbers of sequence, making it appear as if there was substantially more starting material in samples containing low numbers of sequence copies.

The method of the invention also has advantages over present quantification methods such as optical density using an ELISA methodology. As shown above, O.D. may not correlate well with actual numbers of organisms at all levels of concentration.

All articles and patents cited in this application, including those in the following Bibliography, are incorporated herein by reference.

Further modifications, uses, and applications of the invention described herein will be apparent to those skilled in the art. It is intended that such modifications be encompassed in the claims that follow the Bibliography.

BIBLIOGRAPHY

1. Albright, L J, et al., "Strategic management for control of bacterial kidney disease at farmed salmonid sites in coastal British Columbia." Abstract. Proceedings of the Aquaculture International Congress and Exposition, Vancouver, British Columbia, Canada (Sep. 6–9, 1988).
2. "Bacterial Kidney Disease", Report of the Scientific Committee on Animal Health and Animal Welfare, European Commission Health & Consumer Protection Directorate-General (Sanco/B3/Ah/R14/1999) (Adopted Dec. 8, 1999).
3. Fryer, J L, and Sanders, J E, "Bacterial kidney disease of salmonid fish", Annual Review of Microbiology, 35:273–298 (1981).
4. Pascho, R J, et al., "Brood stock segregation of spring chinook salmon *Onchorhynchus tshawytscha* by use of the enzyme-linked immunosorbent assay (ELISA) and the fluorescent antibody technique (FAT) affects the prevalence and levels of *Renibacterium salmoninarum* infection in progeny", Disease of Aquatic Organisms, 12:25–40 (1991).
5. Pascho, R J, et al., "Comparison of the membrane-filtration fluorescent antibody test, the enzyme-linked immunosorbent assay, and the polymerase chain reaction to detect *Renibacterium salmoninarum* in salmonid ovarian fluid", Journal Veterinary Diagnostic Investigation, 10:60–66 (1998).
6. Wiens, G D, and Kaattari, S L, "Bacterial kidney disease (*Renibacterium salmoninarum*)" in Fish Diseases and Disorders, Vol. 3: Viral, Bacterial, and Fungal Infections, P T K Woo and D W Bruno, eds., CABI Publishing, pages 269–301 (1999).
7. Ryman N., and Jorde, P E, "Statistical power when testing for genetic differentiation", Molecular Ecology, 10:2361–2373 (2001).

What is claimed is:

1. A method for detecting the presence or absence of *Renibacterium salmoninarum*, the causative organism of Bacterial Kidney Disease (BKD), in a sample by real-time polymerase chain reaction (PCR) comprising:
   (a) combining the sample, a forward PCR primer that hybridizes to a site on a DNA sequence, wherein the DNA sequence is a portion of the p57 gene of *Renibacterium salmoninarum*, a reverse PCR primer that hybridizes to the DNA sequence at a site which is distinct from the site the DNA sequence to which the forward primer hybridizes, and a probe that hybridizes to a site on the DNA sequence that is between the sites on the DNA sequence to which the forward and reverse primers hybridize, which probe contains a label that provides a change in signal that is related to the number of copies of the DNA sequence that are amplified during each round of PCR, thereby forming a mixture,
   (b) performing one or more rounds of PCR on the mixture,
   (c) and determining the amount of the change in signal of the label, thereby detecting the presence or absence of *Renibacterium salmoninarum* in the sample, wherein the forward PCR primer comprises the sequence of Seq. ID No. 1 or the reverse primer comprises the sequence of Seq. ID No. 2.

2. The method of claim 1 wherein the forward PCR primer comprises the sequence of Seq. ID No. 1.

3. The method of claim 1 wherein the reverse PCR primer comprises the sequence of Seq. ID No. 2.

4. The method of claim 1 wherein the probe comprises the sequence of Seq. ID No. 3.

5. The method of claim 1 wherein the label is a fluorescent label.

6. The method of claim 1 wherein the forward PCR primer comprises the sequence of Seq. ID No. 1 and the reverse PCR primer comprises the sequence of Seq. ID No. 2.

7. The method of claim 6 wherein the probe comprises the sequence of Seq. ID No. 3.

8. The method of claim 7 wherein the label is a fluorescent label.

9. The method of claim 2 wherein the probe comprises the sequence of Seq. ID No. 3.

10. The method of claim 9 wherein the label is a fluorescent label.

11. The method of claim 3 wherein the probe comprises the sequence of Seq. ID No. 3.

12. The method of claim 11 wherein the label is a fluorescent label.

13. A method for detecting the presence or absence of *Renibacterium salmoninarum*, the causative organism of Bacterial Kidney Disease (BKD), in a sample by real-time polymerase chain reaction (PCR) comprising:
   (a) combining the sample, a forward PCR primer that hybridizes to a site on a DNA sequence, wherein the DNA sequence is a portion of the p57 gene of *Renibacterium salmoninarum*, a reverse PCR primer that hybridizes to the DNA sequence at a site which is distinct from the site on the DNA sequence to which the forward primer hybridizes, and a probe that hybridizes to a site on the DNA sequence that is between the sites on the DNA sequence to which the forward and reverse primers hybridize, which probe contains a label that provides a change in signal that is related to the number of copies of the DNA sequence that are amplified during each round of PCR, thereby forming a mixture,
   (b) performing one or more rounds of PCR on the mixture,
   (c) and determining the amount of the change in signal of the label, thereby detecting the presence or absence of *Renibacterium salmoninarum* in the sample, wherein the probe consists of the sequence of Seq. ID No. 3.

14. The method of claim 13 wherein the label is a fluorescent label.

15. A method for detecting the presence or absence of *Renibacterium salmoninarum*, the causative organism of Bacterial Kidney Disease (BKD), in a sample by real-time polymerase chain reaction (PCR) comprising:

(a) combining the sample, a forward PCR primer that hybridizes to a site on a DNA sequence, wherein the DNA sequence is a portion of the p57 gene of *Renibacterium salmoninarum*, a reverse PCR primer that hybridizes to the DNA sequence at a site which is distinct from the site on the DNA sequence to which the forward primer hybridizes, and a probe that hybridizes to a site on the DNA sequence that is between the sites on the DNA sequence to which the forward and reverse primers hybridize, which probe contains a label that provides a change in signal that is related to the number of copies of the DNA sequence that are amplified during each round of PCR, thereby forming a mixture, (b) performing one or more rounds of PCR on the mixture, (c) and determining the amount of the change in signal of the label, thereby detecting the presence or absence of *Renibacterium salmoninarum* in the sample, wherein the forward PCR primer comprises the sequence of Seq. ID No. 1 or the reverse primer comprises the sequence of Seq. ID No. 2 or the probe consists of the sequence of Seq. ID No. 3.

16. The method of claim 15 wherein the label is a fluorescent label.

* * * * *

SEQUENCE LISTING

<160> NUMBER OF SEQ ID NOS: 4
<210> SEQ ID NO 1
<211> LENGTH: 24
<212> TYPE: DNA
<213> ORGANISM: Artificial Sequence
<220> FEATURE:
<223> OTHER INFORMATION: Primer that binds to a cDNA reverse transcri
      bed from the p57 gene of Renibacterium salmoninarum, which has
      been assigned GenBank Accession No. AF 123888

<400> SEQUENCE: 1
caacagggtg    gttattctgc    tttc                                    24

<210> SEQ ID NO 2
<211> LENGTH: 22
<212> TYPE: DNA
<213> ORGANISM: Artificial Sequence
<220> FEATURE:
<223> OTHER INFORMATION: Primer that binds to a cDNA reverse
      transcribed from the p57 gene of Renibacterium salmoninarum,
      which has been assigned GenBank Accession No. AF 123888

<400> SEQUENCE: 2
ctataagagc    caccagctgc    aa                                      22

<210> SEQ ID NO 3
<211> LENGTH: 20
<212> TYPE: DNA

-continued

```
<213> ORGANISM: Artificial Sequence
<220> FEATURE:
<223> OTHER INFORMATION: Probe that binds to a cDNA reverse transcribed
      from the p57 gene of Renibacterium salmoninarum, which has been
      assigned GenBank Accession No. AF 123888

<400> SEQUENCE: 3
ctccagcgcc    gcaggaggac                                               20

<210> SEQ ID NO 4
<211> LENGTH: 95
<212> TYPE: DNA
<213> ORGANISM: Artificial Sequence
<220> FEATURE:
<223> OTHER INFORMATION: Synthetic oligonucleotide that binds to a
      cDNA reverse transcribed from the p57 gene of Renibacterium
      salmoninarum, which has been assigned GenBank Accession No. AF
      123888

<400> SEQUENCE: 4
caacagggtg gttattctgc tttctttcac gagttaaggc                            40
ctgacgggac ctccagcgcc gcaggaggac cagttgcagc                            80
tggtggctct tatag                                                       95
```